United States Patent [19]

Smith et al.

[11] Patent Number: 4,772,626
[45] Date of Patent: Sep. 20, 1988

[54] ANTIHYPERCHOLESTEROLEMIC COMPOUNDS

[75] Inventors: Robert L. Smith, Lansdale; Gerald E. Stokker, Gwyneed Valley, both of Pa.

[73] Assignee: Merck & Co., Inc., Rahway, N.J.

[21] Appl. No.: 824,900

[22] Filed: Jan. 31, 1986

[51] Int. Cl.$^4$ .................. C07D 309/30; A61K 31/365
[52] U.S. Cl. .................................. 514/460; 549/292; 514/824
[58] Field of Search ................. 549/292; 514/460, 824

[56] References Cited

U.S. PATENT DOCUMENTS 4,375,475  3/1983  Willard et al. .
4,459,422  7/1984  Willard et al. .

Primary Examiner—Norma S. Milestone
Attorney, Agent, or Firm—Melvin Winokur; Joseph F. DiPrima

[57] ABSTRACT

Novel 3-hydroxy-3-methylglutaryl-coenzyme A (HMG-CoA) reductase inhibitors which are useful as antihypercholesterolemic agents and are represented by the following general structural formulae (I) and (II):

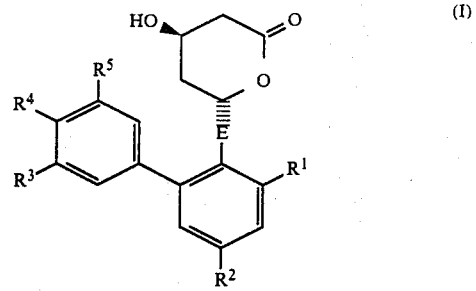

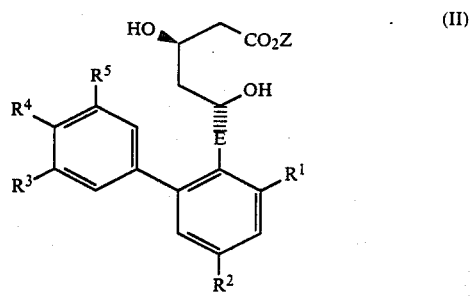

and pharmaceutically acceptable salts of the compounds (II) in which Z is hydrogen are disclosed.

15 Claims, No Drawings

ANTIHYPERCHOLESTEROLEMIC COMPOUNDS

SUMMARY OF THE INVENTION

This invention relates to novel compounds which are HMG-CoA reductase inhibitors and are useful as antihypercholesterolemic agents. Specifically the compounds of this invention are hydroxy alkyl analogs of totally synthetic biphenyl containing antihypercholesterolemic agents. Additionally, pharmaceutical compositions of these novel compounds, as the sole therapeutically active ingredient, and in combination with bile acid sequestrants are disclosed.

DETAILED DESCRIPTION OF THE INVENTION

The specific HMG-CoA reductase inhibitors of this invention are the compounds represented by the following general structural formulae (I) and (II):

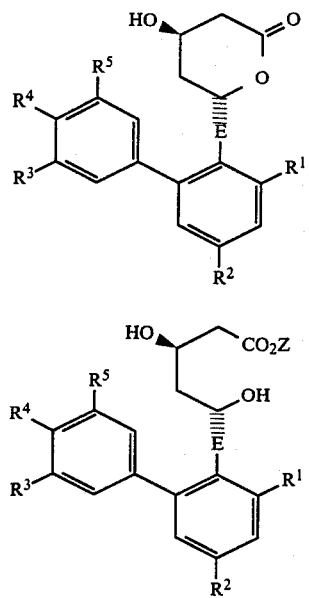

wherein:
E is —CH$_2$CH$_2$— or —CH=CH—; R$^1$, R$^2$, R$^3$, R$^4$ and R$^5$ independently are
  hydrogen;
  halogen (F, Cl, Br or I);
  C$_{1-4}$ alkyl;
  C$_{1-4}$ haloalkyl;
  hydroxy —C$_{1-4}$ alkyl;
  C$_{1-8}$ alkanoyloxy —C$_{1-4}$ alkyl;
  C$_{8-12}$ aralkanoyloxy —C$_{1-4}$ alkyl; or
  C$_7$ or C$_{11}$ aroyloxy —C$_{1-4}$ alkyl;
  with the proviso that at least one of R$^1$, R$^2$, R$^3$, R$^4$ or R$^5$ is selected from
    hydroxy —C$_{1-4}$ alkyl;
    C$_{1-8}$ alkanoyloxy —C$_{1-4}$ alkyl;
    C$_{8-12}$ aralkanoyloxy —C$_{1-4}$ alkyl; or
    C$_7$ or C$_{11}$ aroyloxy —C$_{1-4}$ alkyl;
Z is hydrogen, C$_{1-5}$ alkyl or C$_{1-5}$ alkyl substituted with a member selected from
  phenyl;
  dimethylamino; or
  acetylamino;
and pharmaceutically acceptable salts of the compound (II) in which Z is hydrogen.

One embodiment of this invention are the compounds of the formulae (I) and (II) wherein:
E is —CH$_2$CH$_2$— or —CH=CH—;
R$^1$ and R$^2$ independently are C$_{1-4}$ alkyl or hydroxy —C$_{1-4}$ alkyl;
R$^3$, R$^4$ and R$^5$ independently are hydrogen, fluoro, C$_{1-4}$ alkyl, or hydroxy —C$_{1-4}$ alkyl;
Z is hydrogen, C$_{1-5}$ alkyl or C$_{1-5}$ alkyl substituted with a member selected from
  phenyl;
  dimethylamino; or
  acetylamino;
and pharmaceutically acceptable salts of the compound (II) in which Z is hydrogen. One class of compounds of this embodiment are those compounds of the formulae (I) and (II) wherein E is —CH=CH—. Illustrative of this class of compounds are those compounds of the formulae (I) and (II) wherein R$^1$ and R$^2$ independently are methyl or hydroxymethyl; R$^3$ is methyl or hydroxymethyl; R$^4$ is fluoro, R$^5$ is hydrogen or methyl and Z is hydrogen and pharmaceutically acceptable salts thereof. Exemplifying this class is trans-(E)-6-[2-[4'-fluoro-3'-(hydroxymethyl)-3,5-dimethyl[1,1'-biphenyl]-2-yl]ethenyl]-3,4,5,6-tetrahydro-4-hydroxy-2H-pyran-2-one and its corresponding free hydroxy acid.

The pharmaceutically acceptable salts of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of the formula (I) wherein E is —CH=CH— are conveniently prepared from the appropriately substituted cinnamaldehyde compound (1) according to the following synthetic pathway utilizing the general procedures described in U.S. Pat. Nos. 4,375,475 or 4,459,422 or co-pending patent applications Ser. No. 696,963, filed Jan. 31, 1985, now U.S. Pat. No. 4,611,067; Ser. No. 696,965, filed Jan. 31, 1985, now U.S. Pat. No. 4,582,914, or Ser. No. 741,069 filed June 4, 1985, now abandoned.

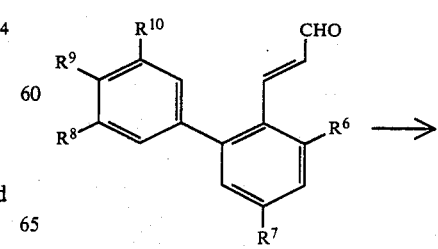

(1)

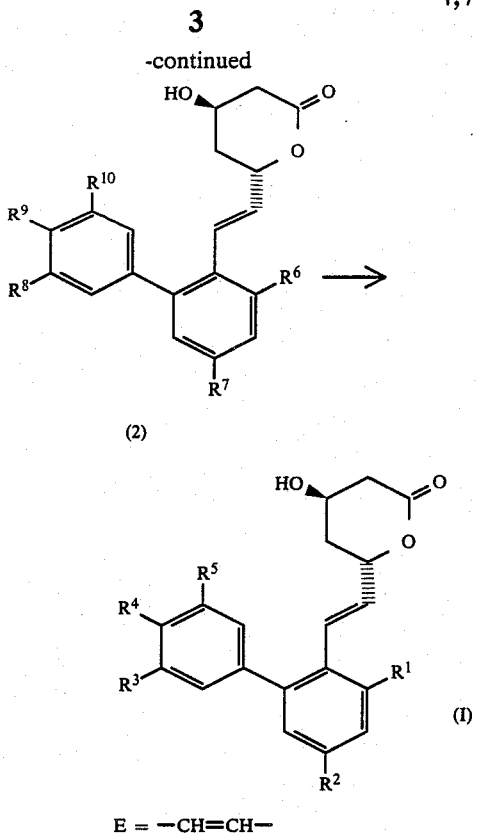

E = —CH=CH—

The cinnamaldehyde compound (1), wherein $R^6$, $R^7$, $R^8$, $R^9$ and $R^{10}$ are defined as $R^1$, $R^2$, $R^3$, $R^4$ and $R^5$, respectively, except that when $R^1$, $R^2$, $R^3$, $R^4$ or $R^5$ is hydroxy —$C_{1-4}$ alkyl that substituent is protected as a tri($C_{1-4}$ alkyl) silyloxy —$C_{1-4}$ alkyl group and the like, is reacted with the dianion of an acetoacetic acid ester, such as methyl or ethyl ester to form a hydroxy-keto ester. The resultant hydroxy-keto ester is then stereospecifically reduced using a trialkyl borane and sodium borohydride in an alcoholic solvent utilizing the general procedure described in co-pending application Ser. No. 725,891 filed Apr. 25, 1985, now U.S. Pat. No. 4,645,854. The resultant dihydroxy ester is saponified and lactonized under standard conditions to afford the compound (2) which is treated with tetrabutylammonium fluoride under standard conditions to remove the tri($C_{1-4}$ alkyl) silyl protecting group to afford the hydroxy —$C_{1-4}$ alkyl substituent, where present in the compounds of formula (I) wherein E is —CH=CH—.

The compounds of the formula (I) wherein E is —$CH_2CH_2$— are conveniently prepared from the compounds of the formula (I) wherein E is —CH=CH— by the reduction of the —CH=CH— bridging group utilizing the general procedure described in U.S. Pat. Nos. 4,375,475 and 4,459,422.

The preparation of the cinnamaldehyde compounds may be accomplished by the general procedures described in U.S. Pat. Nos. 4,375,475 and 4,459,422 or the nickel catalyzed aryl cross coupling procedure described in co-pending patent application Ser. No. 637,081, filed Aug. 1, 1984. Prior to or subsequent to this formation of the biphenyl moiety, a $C_{1-4}$ haloalkyl substituent can be converted to a hydroxy —$C_{1-4}$ alkyl substituent by displacement with an acetate anion followed by hydrolysis. The hydroxy —$C_{1-4}$ alkyl substituent is then protected with a tri($C_{1-4}$ alkyl)silyl halide, such a dimethyl-tert-butylsilyl chloride, or reacted with the appropriate carboxylic acid or acid halide to form the $C_{1-8}$ alkanoyloxy —$C_{1-4}$ alkyl, $C_{8-12}$ aralkanoyloxy —$C_{1-4}$ alkyl or $C_7$ or $C_{11}$ aroyloxy —$C_{1-4}$ alkyl substituents.

The compounds of the formula (II) wherein Z is hydrogen or a pharmaceutically acceptable salt thereof are readily prepared by the mild basic hydrolysis of the lactone moiety of the compounds of formula (I), careful acidification and formation of the appropriate salt utilizing standard procedures.

The compounds of the formula (II) wherein Z is $C_{1-5}$ alkyl or a substituted $C_{1-5}$ alkyl may be conveniently prepared by the procedures described in U.S. Pat. No. 4,342,767.

The resolution of the compounds of the formula (I) into the desired (+)-trans-isomer is accomplished utilizing the general procedure described in U.S. Pat. Nos. 4,375,475 and 4,459,422.

The compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. it is usually desirable to use the oral route. Doses may be varied, depending on the age, severity, body weight and other conditions of human patients but daily dosage for adults is within a range of from about 2 mg to 2000 mg (preferably 20 to 100 mg) which may be given in two to four divided doses. Higher doses may be favorably employed as required.

The compounds of this invention may also be coadministered with pharmaceutically acceptable non-toxic cationic polymer form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic HMG-CoA reductase inhibition activity of the claimed compounds is measured in the in vitro protocol published in *J. Med. Chem.*, 28, p. 347–358 (1985) and described below:

Isolation of HMG-CoA Reductase

Male Holtzman Sprague-Dawley rats (225–250 g) were kept on reversed lighting and fed Purina rat chow containing 3% cholestyramine for 7 days preceding their sacrifice by $CO_2$ asphyxiation. Livers were removed 6 hours into the dark cycle and used immediately to prepare microsomes. HMG-CoA reductase was solubilized from the freshly prepared microsome by the method of Heller and Shrewsbury [*J. Biol. Chem.*, 1976, 251, 3815] and purified through the second ammonium sulfate precipitation step as described by Kleinsek et al, [*Proc. Natl. Acad. Sci* USA, 1977, 74, 1431]. The enzyme preparation was tested for HMG-CoA reductase potency and diluted with 100 mM phosphate buffer (pH 7.2) so that 100 μl of the enzyme solution, when added to the assay control, gave a value of 50,000–60,000 dpm. The enzyme preparation was stored at −80° C.

HMG-CoA Reductase Inhibition Assay

The assay is essentially the procedure of Shefer et al. [*J. Lipid Res.*, 1972, 13, 402]. The complete assay medium contained the following in a total volume of 0.8 ml: phosphate buffer, pH 7.2, 100 mM; $MgCl_2$, 3 mM;

NADP, 3 mM; glucose 6-phosphate, 10 mM; glucose-6-phosphte dehydrogenase, 3 enzyme units; reduced glutahione, 50 mM; HMG-CoA (glutaryl-3-$^{14}$C, New England Nuclear), 0.2 mM (0.1 $\mu$Ci); and partially purified enzyme stock solution, 100 $\mu$l.

Test compounds or compactin (after first being converted to the sodium salt of their dihydroxy acid form in situ by addition of 1 N NaOH (1 equivalent) were added to the assay system in 10-$\mu$l volumes at multiconcentration levels. After a 40-minute incubation at 37° C. to ensure the complete lactionization of mevalonic acid to mevalonolactone, 0.2 ml of the mixture was added to an 0.5×5.0 cm column containing 100–200 mesh BioRex 5, chloride form (Bio-Rad), wetted with distilled water, as described by Alberts et al., [*J. Proc. Natl. Acad. Sci. U.S.A.,* 1980, 77, 3957]. The unreacted [$^{14}$C]HMG-CoA was absorbed on the resin and the [$^{14}$C] mevalonolactone was eluted with distilled water (2×1 ml) directly into 7-ml scintillation vials. Five milliliters of Aquasol-2 (New England Nuclear) was added to each vial, and radioactivity was measured in a Packard Tri Carb Prias scintillation counter. IC$_{50}$ values were determined by plotting percentage inhibition against test compound concentration and fitting a straight line to the resulting data by using the least-squares method. For estimation of relative inhibitory potencies, compactin was assigned a value of 100 and the IC$_{50}$ value of the test compound was compared with that of compactin determined simultaneously.

Representative of the intrinsic HMG-CoA reductase inhibitory activities of the claimed compounds, trans-(E)-6-[2-[4'-fluoro-3'-(hydroxy methyl)-3,5-dimethyl [l,l'biphenyl]-2-yl] ethenyl]3,4,5,6-tetrahydro-4-hydroxy-2H-pyran-2-one possess a relative potency of 26.5 when compared to compactin at 100.

Included within the scope of this invention is the method of treating arteriosclerosis, famifal hypercholesterolemia or hyperlipidemia which comprises administering to a subject in need of such of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of
trans-(E)-6-[2-[4'fluoro-3'(hydroxymethyl)-3,5-dimethyl
[1,1'-biphenyl]-2-yl]ethenyl]3,4,5,6-tetrahydro-4-hydroxy-2H-pyran-2-one (a) 4-Bromo-2-(bromomethyl)-1-fluorobenzene (1a)

To a refluxing solution of 5-bromo-2-fluorotoluene (3.8 g, 20 mmol) in CCl$_4$ (30 mL) illuminated with a 275 W UV-sun lamp, a solution of Br$_2$ (1.1 mL, 20 mmol) in CCl$_4$ (30 mL) was added dropwise. Refluxing and irradiation were continued for an additional 0.5 h and then the clear pale amber solution was concentrated. Distillation of the residue provided the desired compound (1a) as a clear colorless oil; bp 126°–136° C. (15 mm); NMR 4.38 (2 H, s), 6.6–7.7 (3 H, m).

(b) 2-(Acetoxymethyl)-4-bromo-1-fluorobenzene (1b)

Anhydrous sodium acetate (1.65 g, 20 mmol) was added to a solution of the compound (1a) (3 g, 14.6 mmol) in DMF (25 mL) and the reaciton mixture was stirred under N$_2$ on a steam bath for 11 hours. The reaction mixture was cooled and distributed between H$_2$O (200 mL) and Et$_2$O (100 mL). The organic layer was separated and washed with H$_2$O (3×100 mL), dried, filtered and evaporated, leaving the compound (1b) as a nearly colorless oil; NMR 2.08 (3 H, s), 5.08 (2 H, s), 6.7–7.9 (3 H, m).

(c) 5-Bromo-2-fluorobenzylalcohol (1c)

A solution of the compound (1b) (3.2 g, 14.5 mmol), EtOH (20 mL) and 1 N NaOH (20 mL, 20 mmol) was stirred at reflux under N$_2$ for 1.5 hours. The reaction mixture was cooled and distributed between H$_2$O (150 mL) and Et$_2$O (150 mL). The organic layer was separated and washed with H$_2$O (2×100 mL), dried and the clear faint yellow solution was evaporated. Distillation of the residue provided the compound (1c) as a clear colorless oil; bp 82°–87° C. (0.4 mm); NMR 3.3 (H, br s), 4.6 (2 H, s), 6.81 (H$_3$, t, J=9 Hz), 7.15–7.37 (H$_4$, m), 7.44 (H$_6$, dd, J=3 and 6 Hz).

(d) 4-Bromo-1-fluoro-2-[(1,1-dimethylethyl) dimethylsilyl]oxymethyl]benzene (1d)

A mixture of the compound (1c) (1.7 g, 8.3 mmol), tert-butyldimethylsilylchloride (1.8 g, 12 mmol) and imidazole (1.6 g, 24 mmol) in dry DMF (15 mL) was stirred under N$_2$ at 22° C. for 20 hours. The mixture was poured into H$_2$O (200 mL) and extracted with Et$_2$O (2×75 mL). The organic extracts were combined and washed wth 1 N HCl (100 mL), H$_2$O (2×100 mL), sat. NaHCO$_3$ (100 mL), dried, filtered and evaporated. The residual oil was chromatographed on silica gel (hexane) to yield the compound (1d); NMR 0.1 (6 H, s), 0.93 (9 H, s), 4.73 (2 H, s), 6.82 (H$_3$, t, J=9 Hz), 7.15–7.37 (H$_4$, m), 7.55 (H$_6$, dd, J=3 and 6 Hz).

Anal. (C$_{13}$H$_{20}$BrFOSi) H;
Calcd, C=48.90;
Found, C=47.84.

(e) (E)-3-[4'-Fluoro-3,5-dimethyl-3'-[(1,1-di methylethyl)dimethylsilyl]oxymethyl][1,1'biphenyl]-2-yl]-2-propenonitrile (1e)

A Grignard reagent, freshly prepared from the compound (1d) (2.0 g, 6.5 mmol) and magnesium turnings (185 mg, 7.5 mmol) in dry THF (6 mL), was filtered into a dry, N$_2$-purged flask. A 1.33 M solution of ZnBr$_2$ in THF (3 A sieve dried, 2.52 mL, 3.36 mmol) was added over a 2 minute period with vigorous stirring. After ca. 5 minutes, a mixture of 2-bromo-4,6-dimethylcinnamylnitrile (1.26 g, 5.4 mmol) and bis(triphenylphosphine)nickel dichloride (100 mg, 0.16 mmol) was added to the gray slurry and the resultant red-brown mixture was stirred at 35° C. under N$_2$ for 4.5 hours. The reaction mixture was quenched with 1 N HCl (100 mL) and extracted into EtOAc (125 mL). The organic phase was washed with H$_2$O (2×100 mL), dried, filtered and evaporated, leaving the compound (1e) as a brown oil. The residual oil was chromatographed on silica gel (EtOAc-hexane (1:10)) to yield the compound (1e); NMR 0.13 (6 H, s), 0.94 (9 H, s), 2.35 (3 H, s), 2.42 (3 H, s), 4.84 (2 H, s), 5.22 (H, d, J=17 Hz), 6.98–7.39 (6 H, m).

(f)
(E)-3-[4'-Fluoro-3,5-dimethyl-3'-[[(1,1-dimethylethyl)-dimethylsilyl]oxymethyl][1,1'biphenyl]-2-yl]-2-propanal (1f)

To a stirred solution of the compound (1e) (1.1 g, 2.9 mmol) in dry $Et_2O$ (20 mL) at $-15°$ C. under $N_2$ was added a solution of Dibal (2.7 mL, 3.2 mmol) in hexane (20%) over a period of ca. 3 minutes. The cooling bath was removed and the reaction mixture was stirred at ambient temperature for 3 hours. The mixture was cooled to ca. $-10°$ C. and quenched with 5% $H_2SO_4$ (ice-cold, 100 mL). The $Et_2O$ solution was dried over $MgSO_4$ and evaporated and the residual yellow oil was chromatographed on silica gel ($CH_2Cl_2$) to give the compound (1f) as a pale yellow viscous oil; NMR 0.09 (6H, s), 0.91 (9H, s), 2.36 (3H, s), 2.46 (3H, s), 4.81 (2H, s), 6.19 (H, dd, J=7 and Hz), 6.98–7.46 (6H, m), 9.45 (H, d, J=7 Hz).

(g) Methyl (E)-7-(4'-fluoro-3,5-dimethyl-3'-[[(1,1-dimethylethyl)-dimethylsilyl]oxymethyl][1,1'-biphenyl]-2-yl]-3-hydroxy-5-oxo-6-heptenoate (1g)

Methyl acetoacetate (243 μL, 2.26 mmol) was added dropwise to a stirred suspension of sodium hydride (50% oil suspension)(110 mg, 2.26 mmol) in anhydrous THF (10 mL) at 0° C. under $N_2$. The resulting yellow solvent was stirred an additional 15 minutes at 0° C. and then treated with a solution of the compound (1f) (0.83 g, 2.09 mmol) in anhydrous THF (5 mL). The resulting orange solvent was stirred 15 minutes at 0° C. and then quenched by dropwise addition of 1 N HCl (5 mL). The reaction mixture was diluted with $H_2O$ (100 mL) and extracted into $Et_2O$ (150 mL). The organic layer was separated, washed with $H_2O$ (2×100 mL), dried over $MgSO_4$ and filtered. The filtrate was evaporated in vacuo leaving the compound (1g) as a thick yellow oil (1.01 g, 94%); NMR 0.137 (6H, s), 0.948 (9H, s), 2.337 (3H, s), 2.343 (3H, s), 2.578 (2H, dd), 3.455 (2H, s), 3.737 (3H, s), 4.548 (H, m), 4.822 (2H, m), 5.306 (H, dd, J=7 and 16 Hz), 6.489 (H, d, J=16 Hz), 6.97–7.42 (6H, m).

(h) Methyl (E)-7-(4'-fluoro-3,5-dimethyl-3'-[[(1,1-dimethylethyl)-dimethylsilyl]oxymethyl][1,1'-biphenyl]-2-yl]-3,5-dihydroxy-6-heptenoate (1h)

The compound (1g) (1.0 g, 1.96 mmol) was dissolved in dry THF (5 mL) under $N_2$ and then treated with triethylborane (1 M in THF, 2.9 mL, 2.9 mmol). After aging for 5 minutes, the reaction mixture was cooled to $-98°$ C. (MeOH-liq. $N_2$ bath). Sodium borohydride (85 mg, 2.25 mmol) was added followed by MeOH (2 mL) over 5 minutes. After stirring for an additional 0.5 hours, the reaction mixture was allowed to warm to $-60°$ C. and then was quenched by the careful addition of 30% $H_2O_2$ (4 mL) in $H_2O$ (10 mL). The mixture was stirred vigourously at ambient temperature for 0.5 hours and then distributed between 1 N HCl (50 mL) and EtOAc (100 mL). The organic layer was washed with $H_2O$ (2×50 mL), dried, filtered and evaporated to provide the compound (1h) as a pale yellow gum. $^1$H NMR shows an 11:1 ratio of erythro vs threo; NMR 0.12 (6 H, s), 0.93 (9 H, s), 1.42–1.61 (2 H, m), 2.32 (6 H, s), 2.34–2.46 (2 H, m), 3.70 (3 H, s), 4.05–4.15 (H, m), 4.3–4.4 (H, m), 4.7–4.85 (2 H, m), 5.29 (H, dd, J=7 and 16 Hz), 6.43 (H, d, J=16 Hz), and 6.50 (H, d, J=16 Hz).

(i)
trans-(E)-6-[2-[4'-Fluoro-3,5-dimethyl-3'-[[(1,1-dimethylethyl)dimethylsilyl]oxymethyl][1,1'-biphenyl]-2-yl]ethenyl]-3,4,5,6-tetra-hydro-4-hydroxy-2H-pyran-2-one (1i)

A solution of the compound (1h) (900 mg 1.7 mmol), 1 N NaOH (2.5 mL, 2.5 mmol) and MeOH (15 mL) was stirred at 25° C. for 1 hour. The reaction mixture was evaporated in vacuo at 25° C. and the residue was dissolved in $H_2O$ (100 mL). The reaction solvent was acidified with 12 N HCl (1 mL) and extracted with $Et_2O$ (100 mL). The organic extract was washed with $H_2O$ (2×100 mL), dried over $MgSO_4$, filtered, evaporated and the residual crude dihydroxy acid was dissolved in toluene (75 mL) and heated at reflux in a Dean-Stark apparatus. After 3 hours the toluene was removed in vacuo leaving the crude compound (1i) as a thick yellow oil. The oil was chromatographed on silica gel. Elution with $CH_2Cl_2$-acetone (19:1, v=v) to provide the compound (1i) as a pale yellow oil, homogenous by HPLC [time of elution was 3.72 minutes with a flow rate of 4 mL/minutes using 10% isopropanol/hexane on a Whatman Partisil PXS 10/25 PAC column]; NMR 0.139 (6H, s), 0.946 (9H, s), 1.61–1.84 (2H, m), 2.345 (6H, s), 2.45–2.75 (2H, m), 3.947–3.994 (H, m), 4.81 (2H, m), 5.096–5.134 (H, m), 5.30 (H, dd, J=7 and 16 Hz), 6.50 (H, d, J=16 Hz), 6.938–7.338 (6H, m).

(j)
trans(E)-6-[2-[4'-Fluoro-3'-(hydroxymethyl)-3,5-dimethyl[1,1'-biphenyl]-2-yl]ethenyl]-3,4,5,6-tetrahydro-4-hydroxy-2H-pyran-2-one A solution of the compound (1i) (420 mg, 0.087 mmol) in THF (5 mL) was treated with tetrabutylammonium fluoride (1 M in THF, 2.5 mL, 2.5 mmol). After stirring at 20° C. for 5 minutes, 1 N HCl (100 mL) was added and the product was extracted into $Et_2O$ (125 mL). The organic layer was washed with $H_2O$ (2×100 mL), dried, filtered and evaporated to provide the desired compound as a faint yellow gum; homogeneous on TLC [$R_f$ 0.20 vs 0.42 for the silyl ether (silica, $CHCl_3$-MeOH (19:1))] and HPLC [time of elution was 5.36 minutes with a flow rate of 4 mL/min using 20% isopropanol/hexane on a Whatman Partisil PXS 10/25 PAC column]. An analytical sample was crystallized from nBuCl: mp 137°–138° C.; NMR 1.7–1.95 (2 H, m), 2.33 (6 H, s), 2.45–2.75 (2 H, m), 4.05–4.1 (H, m), 4.7–4.85 (2 H, m), 5.12–5.18 (H, m), 5.4 (H, dd, J=7 and 15 Hz), 6.53 (H, d, J=15 Hz), 6.95–7.35 (6 H, m).

EXAMPLES 2 TO 10

Utilizing the general procedures from Example 1 the following compounds are prepared from the appropriately substituted cinnamylnitrile.

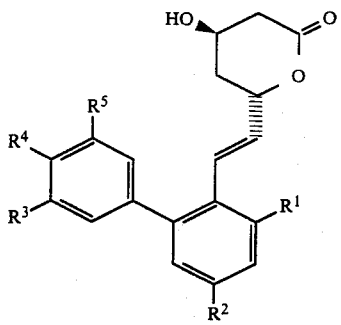

| Compound | R¹ | R² | R³ | R⁴ | R⁵ |
|---|---|---|---|---|---|
| 2 | CH₂OH | CH₃ | CH₃ | F | H |
| 3 | CH₃ | CH₂OH | CH₃ | F | H |
| 4 | CH₃ | CH₃ | CH₂OH | H | CH₃ |
| 5 | CH₃ | CH₂OH | CH₃ | H | CH₃ |
| 6 | CH₂OH | CH₃ | CH₃ | H | CH₃ |
| 7 | CH₃ | CH₃ | CH₂OH | H | CH₃ |
| 8 | CH₃ | CH₃ | CH₂OCC(CH₃)₃ (O) | F | H |
| 9 | C₂H₅ | C₂H₄OH | CH₃ | F | H |
| 10 | C₂H₅ | C₂H₅ | C₂H₄OH | F | H |

EXAMPLE 11

Preparation of Alkali and Alkaline Earth Salts of Compound II

To a solution of the lactone from Example 1(j) (42 mg) in ethanol (2 ml) is added aqueous NaOH (1 equivalent). After one hour at room temperature, the mixture is taken to dryness in vacuo to yield the sodium salt of Compound II.

In like manner, the potassium salt is prepared using one equivalent of potassium hydroxide, and the calcium slat using one equivalent of CaO.

EXAMPLE 12

Preparation of Methyl Ester of Compound II

To a solution of 400 mg of the lactone from Example 1(d) in 100 ml of absolute methanol is added 10 ml 0.1 M sodium methoxide in absolute methanol. This solution is allowed to stand at room temperature for one hour, is then diluted with water and extracted twice with ethyl acetate; the ethyl acetate, dried over anhydrous sodium sulfate, is removed in vacuo to yield the methyl ester of Compound II.

In like manner, by the use of equivalent amounts of propanol, butanol, isobutanol, t-butanol, amylalcohol, isoamylalcohol, 2-dimethylaminoethanol, benzylalcohol, phnethanol, 2-acetamidoethanol, and the like, the corresponding esters are obtained.

EXAMPLE 13

Preparation of free Hydroxy Acids

The sodium salt of the compound II from Example 11 is redissolved in 2 ml of ethanol-water (1:1) and added to 10 ml of IN hydrochloric acid from which the hydroxy acid is extracted with ethyl acetate. The latter solvent is washed once with water, dried, and removed in vacuo with a bath temperature not exceeding 30° C.

The hydroxy acid derived slowly reverts to the lactone on standing.

EXAMPLE 14

As a specific embodiment of a composition of this invention, 20 mg of the lactone from Example 1(j) is formulated with sufficient finely divided lactose to provide a total amount of 580 to 590 mg to fill a size 0 hard gelatin capsule.

What is claimed:

1. A compound represented by the following general structural formula (I):

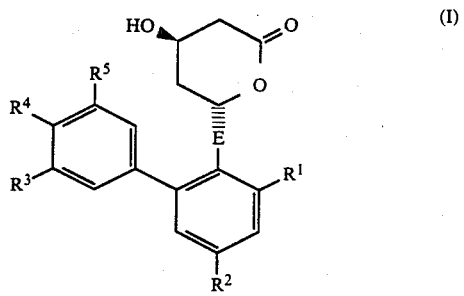

wherein:

E is —CH₂CH₂— or —CH=CH—;

R¹ and R² independently are methyl or hydroxymethyl; and

R³ and R⁵ independently are hydrogen, methyl, hydroxymethyl, or C₁₋₈alkanoyloxymethyl; and R⁴ is fluoro or hydrogen; with the proviso that at least one of R¹, R², R³ or R⁵ is selected from hydroxymethyl or C₁₋₈ alkanoyloxymethyl.

2. A compound according to claim 1 wherein: E is —CH=CH—.

3. A compound according to claim 2 wherein:
R³ is methyl or hydroxymethyl;
R⁴ is fluoro;
R⁵ is hydrogen or methyl.

4. A compound according to claim 3 which is trans-(E)-6-[2-[4'fluoro-3'-(hydroxymethyl)-3,5-dimethyl [1,1'-biphenyl]-2-yl]ethenyl]-3,4,5,6-tetrahydro-4-hydroxy-2H-pyran-2-one.

5. A compound according to claim 1 which is the (+)-trans-isomer.

6. A pharmaceutical composition comprising a nontoxic hypocholesterolemic, hypolipidemic amount of a compound according to claim 1 and a pharmaceutically acceptable carrier.

7. A pharmaceutical composition according to claim 6 wherein:
E is —CH=CH—.

8. A pharmaceutical composition according to claim 7 wherein:
R³ is methyl or hydroxymethyl;
R⁴ is fluoro;
R⁵ is hydrogen or methyl.

9. A pharmaceutical composition according to claim 8 wherein the therapeutically active ingredient is trans-(E)-6-[2-[4'-fluoro-3'-(hydroxymethyl)-3,5-dimethyl [1,1'-biphenyl]-2-yl]ethenyl]-3,4,5,6-tetrahydro-4-hydroxy-2H-pyran-2-one.

10. A pharmaceutical composition according to claim 6 wherein the therapeutically active ingredient is the (+)-trans-isomer.

11. A method of inhibiting cholesterol biosynthesis comprising the administration to a subject in need of such treatment a non-toxic effective cholesterol biosynthesis inhibiting amount of a compound according to claim 1.

12. A method of claim 11 wherein:
E is —CH=CH—.

13. A method of claim 12 wherein:
$R^3$ is methyl or hydroxymethyl;
$R^4$ is fluoro;
$R^5$ is hydrogen or methyl.

14. A method of claim 13 wherein the therapeutically active ingredient is trans-(E)-6-[2-[4'-fluoro-3'-(hydroxymethyl)-3,5-dimethyl[1,1'-biphenyl]-2-yl]ethenyl]-3,4,5,6-tetrahydro-4-hydroxy-2H-pyran-2-one.

15. A method of claim 11 wherein the therapeutically active ingredient is the (+)-trans-isomer.

* * * * *